United States Patent
Johnson et al.

(10) Patent No.: US 10,980,475 B2
(45) Date of Patent: Apr. 20, 2021

(54) METHOD OF SAMPLING SYSTEMIC BIOMARKERS

(71) Applicant: Bohnas Innovations LLC, Coeur d'Alene, ID (US)

(72) Inventors: Casey Johnson, Coeur d'Alene, ID (US); Doran Thomas, Post Falls, ID (US); Greg Bauer, Post Falls, ID (US)

(73) Assignee: Bohnas Innovations LLC, Coeur d'Alene, ID (US)

( * ) Notice: Subject to any disclaimer, the term of this patent is extended or adjusted under 35 U.S.C. 154(b) by 0 days.

(21) Appl. No.: 16/433,904

(22) Filed: Jun. 6, 2019

(65) Prior Publication Data
US 2019/0282161 A1  Sep. 19, 2019

Related U.S. Application Data

(63) Continuation of application No. 16/422,447, filed on May 24, 2019, now abandoned, which is a continuation of application No. 14/726,322, filed on May 29, 2015, now abandoned.

(51) Int. Cl.
*A61B 5/097* (2006.01)
*A61B 5/083* (2006.01)
*A61B 5/00* (2006.01)

(52) U.S. Cl.
CPC .......... *A61B 5/4821* (2013.01); *A61B 5/0836* (2013.01); *A61B 5/097* (2013.01)

(58) Field of Classification Search
None
See application file for complete search history.

(56) References Cited

U.S. PATENT DOCUMENTS

| | | | |
|---|---|---|---|
| 4,677,987 A * | 7/1987 | Choksi | A61B 5/097 422/84 |
| 6,974,321 B2 | 12/2005 | Hirsch et al. | |
| 7,243,649 B2 | 7/2007 | Moenning et al. | |
| 9,138,169 B2 | 9/2015 | Beard | |
| 9,808,182 B2 | 11/2017 | Johnson et al. | |
| 2003/0134253 A1 | 7/2003 | Hirsch et al. | |
| 2004/0102711 A1 | 5/2004 | Wall | |
| 2004/0230108 A1 | 11/2004 | Melker et al. | |
| 2012/0271187 A1 | 10/2012 | Mcneill | |

(Continued)

OTHER PUBLICATIONS

Office Action for U.S. Appl. No. 14/726,322, dated Jan. 25, 2019, Casey Johnson, "Method of Sampling Systemic Biomarkers", 14 pages.

(Continued)

*Primary Examiner* — Kaylee R Wilson
*Assistant Examiner* — Jay B Shah
(74) *Attorney, Agent, or Firm* — Lee & Hayes, P.C.

(57) ABSTRACT

A method including a step of preparing a sampling apparatus for use. The sampling apparatus includes a tubular member having an opening on a distal end thereof. An orientation of the distal end of the tubular member is shapeable. The distal end is substantially rigid so as to maintain a manipulated shape after a direct application of a threshold level of force on the distal end of the tubular member. The tubular member also includes a joint member disposed on a proximal end of the tubular member. The joint member is configured to connect the tubular member to a systemic biomarker sampling device.

5 Claims, 11 Drawing Sheets

(56) References Cited

U.S. PATENT DOCUMENTS

| | | | |
|---|---|---|---|
| 2012/0302908 A1* | 11/2012 | Hemnes | A61B 5/082 600/532 |
| 2013/0190639 A1* | 7/2013 | Kline | A61B 5/082 600/532 |
| 2014/0018691 A1 | 1/2014 | McNeill | |
| 2014/0162209 A1 | 6/2014 | Nguyen et al. | |
| 2014/0182398 A1* | 7/2014 | Colman | A61M 39/1011 73/863.23 |
| 2014/0212838 A1 | 7/2014 | Nguyen et al. | |
| 2014/0212841 A1 | 7/2014 | Nguyen et al. | |
| 2014/0332005 A1* | 11/2014 | Kunz | A61M 16/0666 128/205.25 |
| 2015/0101600 A1 | 4/2015 | Miller et al. | |
| 2015/0335409 A1 | 11/2015 | Hirsch | |
| 2016/0345863 A1 | 12/2016 | Johnson et al. | |
| 2016/0345864 A1 | 12/2016 | Johnson et al. | |
| 2016/0345894 A1 | 12/2016 | Johnson et al. | |
| 2017/0238815 A1* | 8/2017 | Luxon | A61B 5/0205 |

OTHER PUBLICATIONS

Office Action for U.S. Appl. No. 12/726,310, dated Dec. 11, 2018, Johnson et al, "Breath Sampling Apparatus and Method Therefor", 7 pages.

Office Action for U.S. Appl. No. 14/726,322, dated Dec. 14, 2017, Casey Johnson, "Method of Sampling Systemic Biomarkers", 13 pages.

Office Action for U.S. Appl. No. 14/726,310, dated Feb. 7, 2018, Casey Johnson, "Breath Sampling Apparatus and Method Therefor", 6 pages.

Office Action for U.S. Appl. No. 14/726,322, dated Jun. 26, 2017, Johnson et al., "Method of Sampling Systemic Biomarkers", 13 pages.

Office Action for U.S. Appl. No. 14/726,320, dated Jul. 7, 2017, Johnson et al., "Systemic Biomarker Sampling Apparatus ", 11 pages.

Office Action for U.S. Appl. No. 14/726,310, dated Sep. 10, 2018, Casey Johnson, "Breath Sampling Apparatus and Method Therefor", 6 pages.

"Safe Sedate Dental Nasal Mask Instructions", retrieved on Mar. 21, 2017 at <<http://safesedate.com/wp-content/uploads/2014/03/Safe_Sedate_Instructions.pdf>>, Med-Dent Safety and Supply Co., Mar. 2014, pp. 1-4.

Strimbu, et al., "What are Biomarkers?", Current Opinion in HIV and AIDS, Nov. 2010, 6 pages.

\* cited by examiner

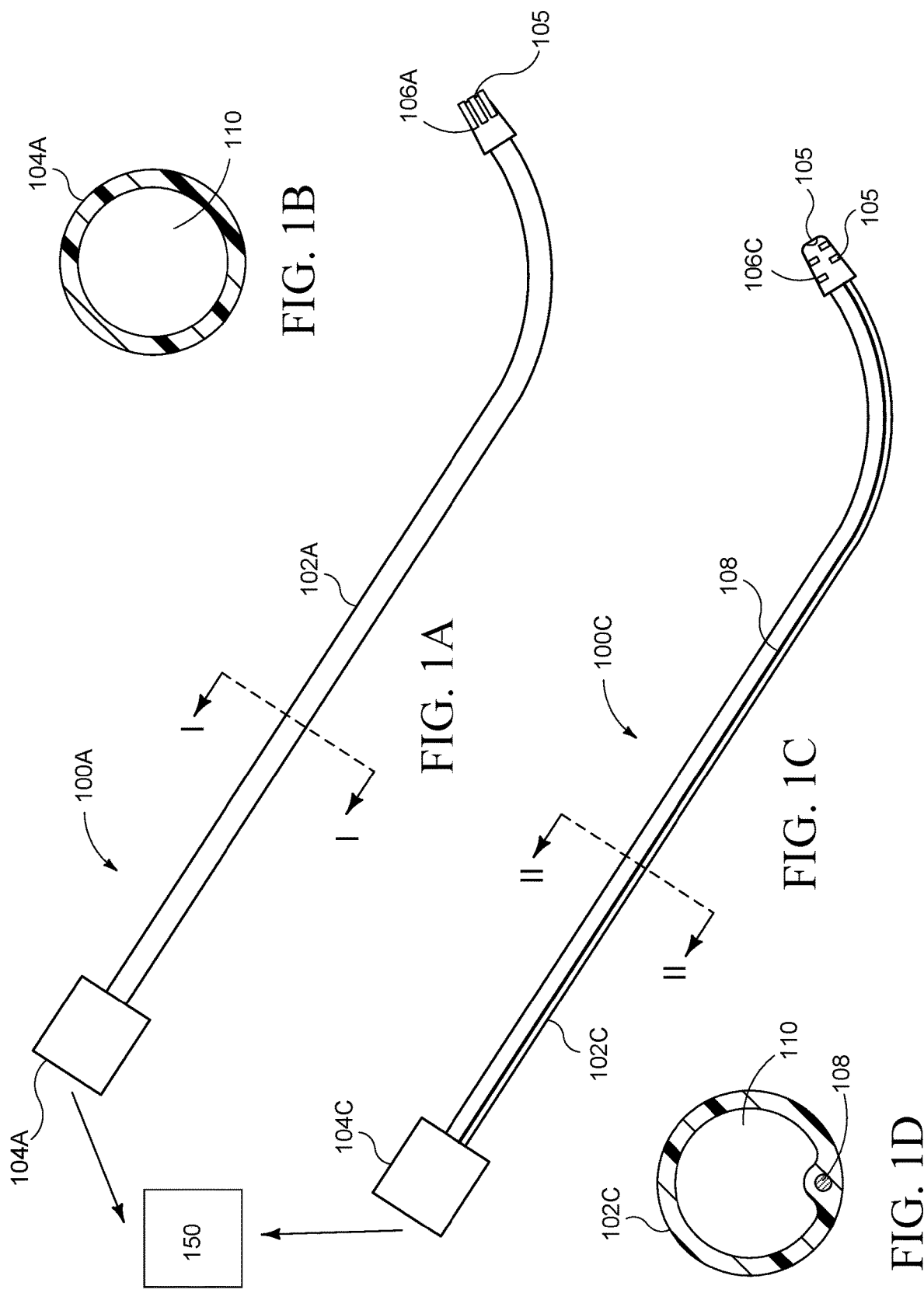

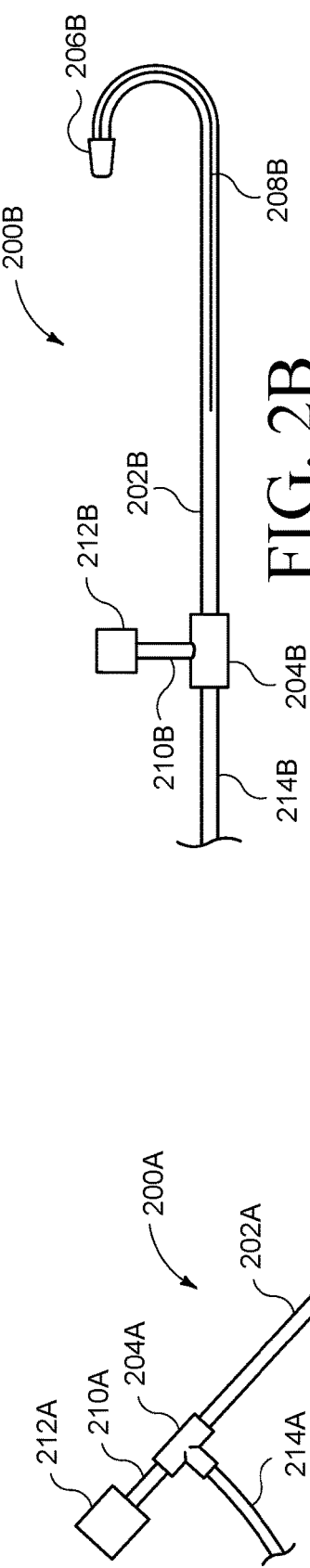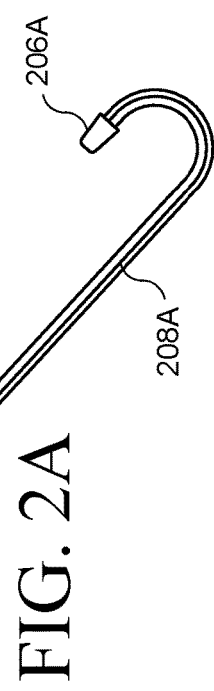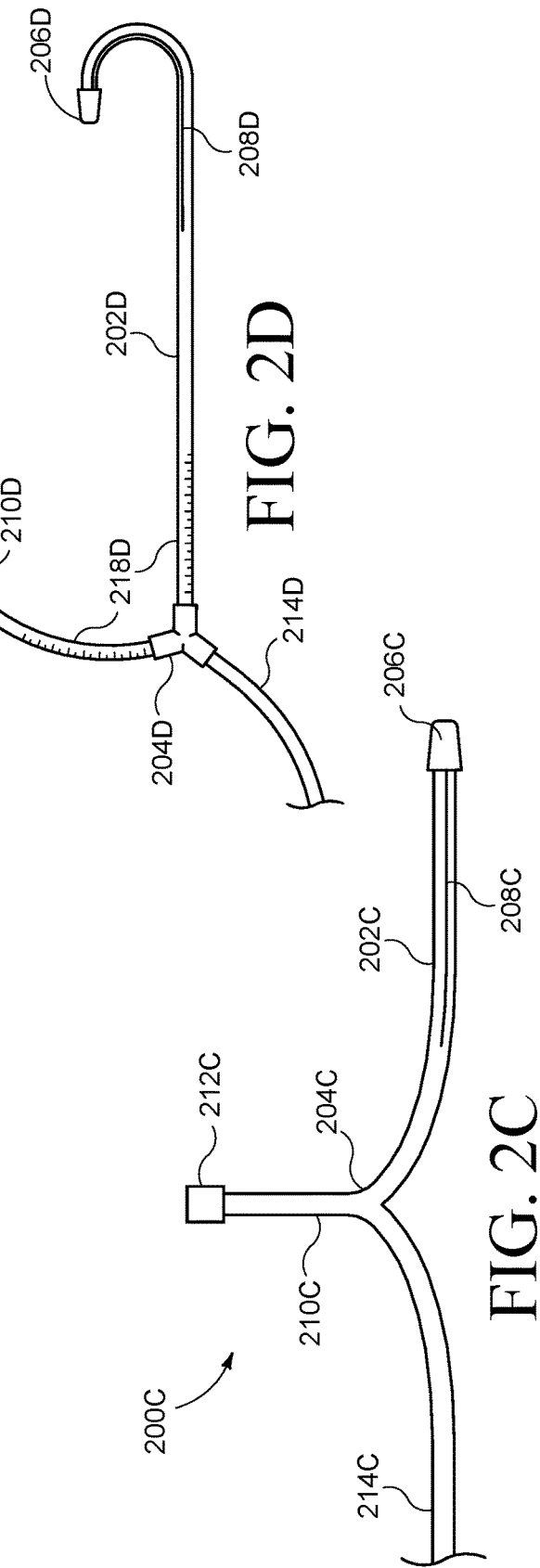

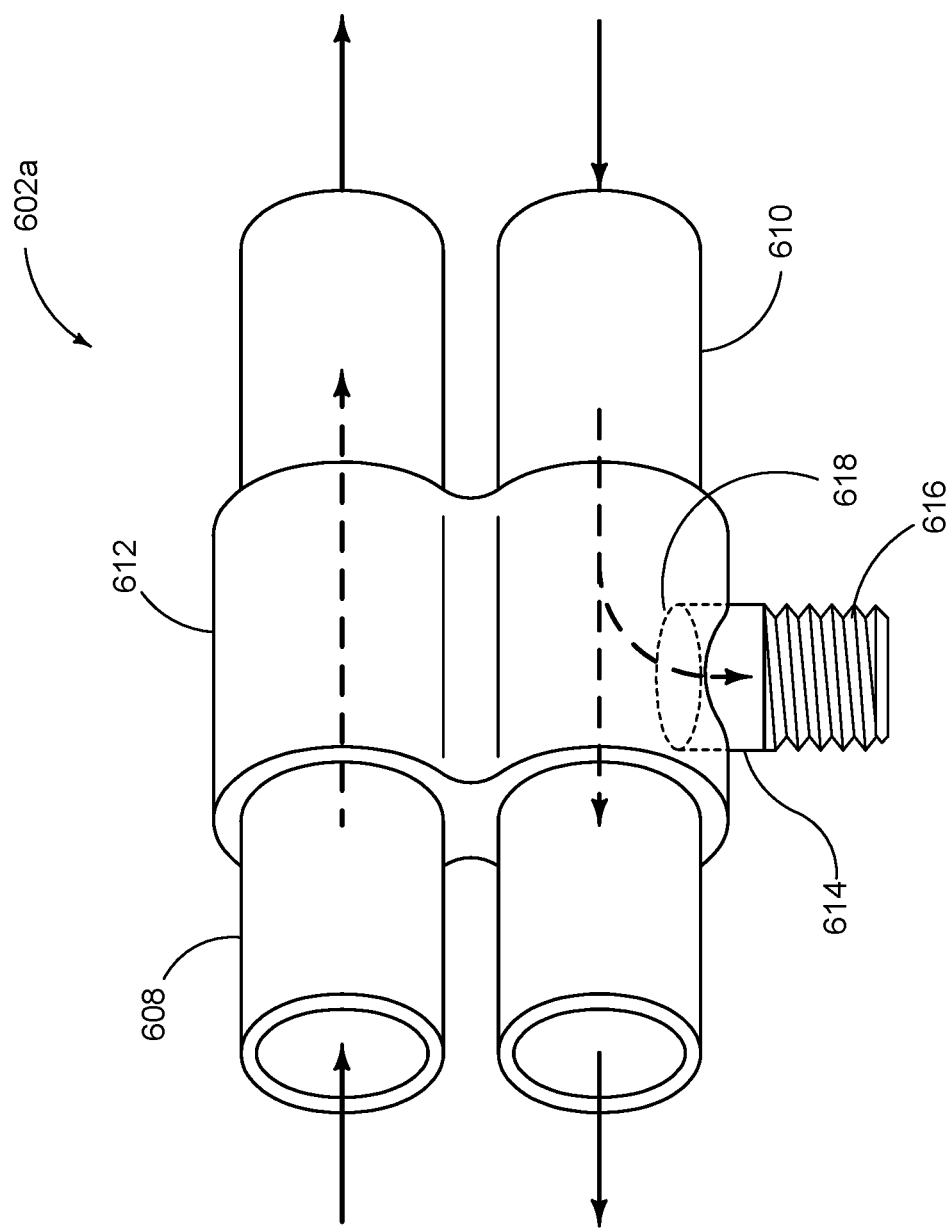

METHOD OF SAMPLING SYSTEMIC BIOMARKERS

RELATED APPLICATIONS

This application claims priority to and is a continuation of U.S. patent application Ser. No. 16/422,447, filed on May 24, 2019, which is a continuation of U.S. patent application Ser. No. 14/726,322, filed on May 29, 2015, the entire contents of which are incorporated herein by reference.

BACKGROUND

In dental procedures during which either sedation or General Anesthesia (GA) is required, a patient may wear a nasal mask or hood via which a gas, such as oxygen or nitrous oxide, is administered to the patient. The nasal mask or hood may be a non-latex, soft, thermal plastic elastomer that covers the nose and is secured to the face via a gravitational pull of a bilateral inspiratory and gas scavenging suction system that hangs from around the patient's head and over the nose while in the recumbent position. Alternatively, other methods of sedation are accomplished without a nasal hood, such as a combination of nasal cannula for oxygen with oral, intramuscular, or submucosal modes of anesthetic delivery. During procedures that deliver anesthetics, it is important that the patient's airway and the delivery of gases are monitored closely because, in some instances, the effects of sedatives, narcotics, and the majority of general anesthetics decrease respiratory drive and can cause brief or prolonged periods of apnea.

It is well documented and widely accepted that the implementation of capnography increases the margin of safety for delivery of anesthesia. Capnography is the monitoring of the concentration of end tidal carbon dioxide ("$ETCO_2$") or exhaled carbon dioxide ("$CO_2$") of a patient in order to assess the physiological status and/or determine the adequacy of ventilation when under anesthesia. Nevertheless, due to the currently existing difficulties associated with monitoring $ETCO_2$, particularly within dentistry due to the tools and work occurring in the mouth of the patient, practitioners do not commonly monitor $ETCO_2$.

In addition to monitoring $ETCO_2$, operators may be further interested in accurately sampling for and/or detecting the levels of other systemic biomarkers found within exhaled breath of a person under sedation or GA in order to assess a patient's status. Therefore, a means to accurately detect and monitor systemic biomarkers, such as $ETCO_2$, within exhaled breath is desirable.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. Furthermore, the drawings may be considered as providing an approximate depiction of the relative sizes of the individual components within individual figures. However, the drawings are not to scale, and the relative sizes of the individual components, both within individual figures and between the different figures, may vary from what is depicted. In particular, some of the figures may depict components as a certain size or shape, while other figures may depict the same components on a larger scale or differently shaped for the sake of clarity.

FIG. 1A illustrates a side view of an example of an exhaled breath sampling apparatus.

FIG. 1B illustrates a front cross-sectional view at line I-I of the tubular member of the example exhaled breath sampling apparatus in FIG. 1A.

FIG. 1C illustrates a side view of another example of an exhaled breath sampling apparatus.

FIG. 1D illustrates a front cross-sectional view at line II-II of the tubular member of the example exhaled breath sampling apparatus in FIG. 1D.

FIG. 2A illustrates a side view of another example of an exhaled breath sampling apparatus.

FIG. 2B illustrates a side view of another example of an exhaled breath sampling apparatus.

FIG. 2C illustrates a side view of another example of an exhaled breath sampling apparatus.

FIG. 2D illustrates a side view of another example of an exhaled breath sampling apparatus.

FIG. 6B illustrates the connector component of FIG. 6A.

DETAILED DESCRIPTION

Overview

Figure 3A:
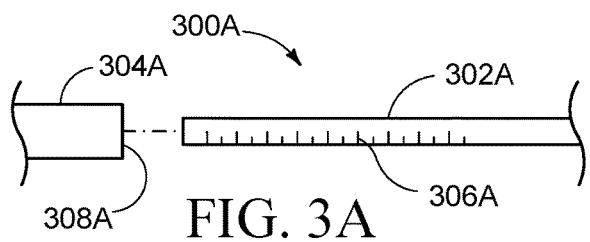
FIG. 3A illustrates an exploded, side view of an example of a proximal end of a tubular member of an exhaled breath sampling apparatus.

This disclosure is directed to a method and apparatus that may be used in monitoring the presence of and/or concentration of a systemic biomarker, such as $ETCO_2$ or exhaled $CO_2$, in the exhaled breath of a patient, in order to assess the physiological status and/or determine the adequacy of ventilation during a procedure that may involve sedation or GA. The embodiments are described with specificity in order to meet statutory requirements. However, the description itself is not intended to limit the scope of this patent. Rather, the inventors have contemplated that the claimed invention might also be embodied in other ways, to include different elements or combinations of elements similar to the ones described in this document, in conjunction with other present or future technologies.

The sampling apparatus described herein may be structured to be inserted into a patient's mouth and/or connect to another device to sample exhaled breath from a patient's nose and/or mouth. Accordingly, the sampling apparatus may include a tubular member (also called "a sampling line") and a connector attached to the tubular member. The tubular member permits the flow of exhaled breath to go from the patient to a monitoring device, where a systemic biomarker, such as $ETCO_2$ exhaled by the patient, is monitored for the safety of the patient. Systemic biomarkers may include, for example, $ETCO_2$, nitric oxide, moisture, humidity, temperature, acids, ketones, or other gases, elements, or characteristics found in or associated with exhaled human breath. A biomarker that may be particularly useful is $CO_2$, since the average indoor $CO_2$ levels range from 400-2000 ppm, whereas exhaled $CO_2$ levels range around 38,000 ppm.

The tubular member may be manufactured such that at least a portion thereof is manipulable and has plastic material properties so as to be deformable continuously and permanently in any direction without rupture. This manipulable feature provides the operator of the apparatus, e.g., the anesthesiologist, dentist, or other medical personnel, the ability to alter the shape and orientation of the apparatus to better position apparatus where it may more consistently monitor the systemic biomarker, such as $ETCO_2$.

Other advantages of the sampling apparatus relate to its versatility including, but not limited to, being connectable to or integral with, a nasal mask, a nasal hood, an oral airway, and a dental Isolite® system. Furthermore, in embodiments described below, the sampling apparatus samples exhaled air from both the nose and mouth. An additional advantage is that in embodiments, a length of the sampling apparatus may be quickly and easily adjustable to accommodate the different sizes of patients.

Various embodiments allow for different means of connection between the components of the sampling apparatus itself, between the sampling apparatus and the systemic biomarker sampling device, and the sampling apparatus and the procedural apparatus with which the sampling apparatus may be coupled.

Sometimes, using the current methods of practice monitoring $ETCO_2$ during a procedure, issues and problems related to reliability, and potentially dangerous situations occur. Moreover, patients may even alternate breathing through the nose and the mouth. In such an instance, a nasal sampling line alone will not reliably sample and/or detect exhaled air coming from the mouth. The sampling apparatus of the instant application helps to eliminate or minimize the occurrence of such situations. Namely, the sampling apparatus helps to avoid kinking or occlusions of the sampling line (which may be crafted from, for example, intravenous catheter or extension tubing). Further, the sampling apparatus may eliminate the situation where sampling line is taped to the patient's facial skin. In some instances, hypodermic needles are broken during current procedures and used to puncture the nasal mask so as to insert tubing therein and sample the $CO_2$. In such situations, the patient may be subject to a possible cut or abrasion from the broken end of the needle. Accordingly, the embodiments of the sampling apparatus of the instant application, as detailed herein, may provide several advantages over the current methods of monitoring $CO_2$.

Multiple embodiments of an apparatus that may be used to achieve the desired effects of the instant application, including the ability to reliably sample and detect a systemic biomarker, such as $CO_2$, are described herein below with respect to FIGS. 1A-9B. Note, throughout the specification the terms "proximal" and "distal" appear several times. Unless otherwise specified, "proximal" refers to the side of the sampling apparatus closer to the end that connects to the systemic biomarker sampling device 150 (FIGS. 1A and 1C), such as an $ETCO_2$ monitor, and "distal" refers to the side of the apparatus closer to the opposite end of the sampling apparatus which receives the exhaled breath from the patient.

First and Second Illustrative Embodiments

Inasmuch as the features of FIGS. 1A and 1C are substantially similar, the components of each figure are herein below discussed simultaneously, with the exception of any specific feature that is unique to either one of the figures. Accordingly, substantially similar components are described as, for example, "connector 102A, 102C," which indicates that the connector on each of the figures may be generically described, insofar as they are similar unless explicitly stated otherwise.

Thus, FIGS. 1A-1D illustrate an example sampling apparatus 100A, 100C that may include a tubular member 102A, 102C having a plurality of openings 105 (fenestrations) on the distal end, via which exhaled breath may be sampled from a patient. It is noted that for the sake of simplicity in the drawings, only FIGS. 1A and 1C show an embodiment including a plurality of openings 105 in the distal end of the device. Nevertheless, it is contemplated that any of the embodiments shown or discussed in this application may include either a single opening or more than one opening. Although it may be possible to use a device of the instant application that only has one opening 105, there may be advantages to having a plurality of openings 105, which may not be achievable with a single opening.

The tubular member 102A, 102C may be a piece of tubing, for example, of medical grade tubing. A connector 104A, 104C may be attached to a proximal end of the tubular member 102A, 102C. The connector 104A, 104C may connect to an extension tube (not shown) leading to a systemic biomarker sampling device 150, or may directly connect to the sampling device. The means of connection implemented by the connector 104A, 104C may vary according to user preference, method of manufacture, or common connections available such as a Luer-Lok® type of connection, for example. See some additional examples of types of connections considered in FIGS. 3A-4E. When in use, a pump or other means may create a suction force through the tubular member 102A, 102C to sample the patient's breath through the tubular member 102A, 102C at the sampling device, whereby the sampling device may monitor a level of a biomarker, such as $ETCO_2$, within the breath.

Additionally, the apparatus 100A, 100C may include a cap 106A, 106C having one or more corresponding openings therethrough and may be disposed to align with the one or more openings 105 on the distal end of the tubular member 102A, 102C. The cap 106C, as shown in FIG. 1C, may have a soft, gradual, rounded edge on the distal end thereof, and may be tapered in the longitudinal direction thereof such that the cross-sectional area of the proximal end of the cap 106C is larger than the cross-sectional area of the distal end of the cap 106C. The tapered and rounded features of cap 106C may serve multiple purposes, including, but not limited to comfort of the patient on which the apparatus is used and convenience of the operator, respectively. For example, the soft, rounded edges on the distal end of the cap may prevent harm or annoyance to a patient when placed in a patient's mouth or near the patient's face, when compared with a tube having a rough edge. Further, as discussed in greater detail below, the tapered shape may act as a connector in embodiments, as it creates a wider proximal area on the cap than the distal area of the cap. The wider surface area surrounding the tubular member may act as a backstopping surface to prevent accidental removal of the tubular member (described in greater detail herein below with respect to FIG. 7). Alternatively, the tubular member 102A, 102C may not have a cap, and instead the distal end of the tubular member may be shaped in a tapered manner itself or may be left as originally manufactured (not shown). In the case where no cap is used, the risk of having the cap come off and enter the patient's body is eliminated.

In the embodiments shown in FIGS. 1A and 1C, the respective distal ends thereof are bent such that the distal end is oriented transversely to a main direction of extension of the majority of the tubular member 102A, 102C. Note, however, the tubular members 102A, 102C may be temporarily pre-shaped during manufacturing to be straight or to include a curved or hooked shape, for example, which may ease the placement of the tubular member 102A, 102C within a patient's mouth at the time of use in a manner that is out of the way of the work being done in the patient's mouth.

Additionally and/or alternatively, the tubular member 102A, 102C may include a manipulable characteristic or component, so that a least a portion of the tubular member 102A, 102C is shapeable and yet substantially rigid so as to maintain a manipulated shape upon a direct application of a threshold level of force on the portion of the tubular member 102A, 102C. The threshold force, which may be applied by an operator to alter the shape of the portion of the tubular member 102A, 102C, is that force sufficient to overcome the inherent resistance force from a property of rigidity associated with the chosen material that is used to manufacture the manipulable characteristic of the tubular member 102A, 102C. The term "substantially rigid" is intended to convey the meaning that, while the orientation of the tubular member 102A, 102C may be altered under a deliberate act of a threshold force by an operator, the rigidity of the tubular member 102A, 102C is such that it is not so limp or flimsy as to bend and flex into a different orientation under the mere presence of a gravitational force, for example, when lifted or shifted from a resting state.

As an example of the manipulable characteristic or component, in FIG. 1A, the material of the tubular member 102A may have properties such that a shape of the tubular member 102A itself is manipulable due to the material forming the tubular member 102A. Materials that may be used for the manipulable material may include, for example, ductile or malleable metals such as aluminum, pliable plastics, rubber, and some ceramics, or a combination thereof.

In an alternative example embodiment, instead of, or in addition to, the material of the tubular member itself being manipulable, a distinct manipulable member 108 may be molded, manufactured, embedded, inserted, or otherwise attached to either an inside or an outside of the wall of the tubular member 102C, or disposed within the wall of the tubular member 102C, as shown in FIG. 1C. For example, the manipulable member 108 may be disposed in the wall of the tubular member 102C adjacent lumen 110. Similar to having a manipulable material, as described with respect to FIG. 1A, the manipulable member 108 enables the operator to adjust the size, shape, position, and/or direction of extension of at least the distal end of the tubular member 102C, so as to be able to place the tubular member 102C within, on, or around the mouth of a patient.

In embodiments, the manipulable member 108 may include a wire, rod, strip, bar, or another section of metal, plastic, ceramic, rubber, or other suitable material. The material of the manipulable member 108 may be such that the manipulable member 108 is pliable and, when the apparatus 100C is used to sample and/or detect a biomarker during a procedure, the manipulable member 108 may be manipulated to form a curved distal end, such as a quarter round, or a hook shape, if the operator desires. Additionally, the length of the manipulable member 108 may be such that the manipulable member 108 extends:

1) throughout the entire length of the tubular member 102C;

2) at least along the distal end of the tubular member 102C (see for example FIGS. 2A-2D); or 3) for a portion less than the entire length of the tubular member 102C and located away from the ends thereof, such as at a middle portion between the distal and proximal ends (not shown).

An advantage of the manipulable member 108 in the distal end of the tubular member 102A, 102C is that the operator may place the sampling apparatus 100A, 100C between a patient's teeth and cheek so that the mouth cavity is free of obstructions during the procedure. Thusly, the distal end of the tubular member 102A, 102C is positioned to suction the patient's breath and monitor a predetermined biomarker in the breath via the intake into lumen 110.

Inasmuch as the manipulable member 108 is adjacent the first lumen 110, the manipulable member 108 may be disposed in a second lumen in the wall of lumen 110 so as to extend parallel with lumen 110, as shown more clearly in FIG. 1D. As indicated above, alternatively, the manipulable member 108 may be attached directly to an inner surface of the lumen 110 or an outer surface of the tubular member 102C; or the manipulable member 108 may simply be embedded in the wall of the lumen 110, as it appears in FIG. 1D.

In comparison, FIG. 1B shows a cross-sectional view of the tubular member 102A in FIG. 1A as a solitary lumen having a substantially uniform wall thickness, whereas FIG. 1D shows a cross-sectional view of tubular member 102C with lumen 110 as a first lumen, or a solitary lumen, and manipulable member 108 embedded in the wall or inserted into a second lumen large enough to secure the manipulable member 108.

Third-Sixth Illustrative Embodiments

In FIGS. 2A-2D, various alternative embodiments of the sampling apparatus 200A-200D are shown. Inasmuch as several of the features found in the various embodiments of FIGS. 2A-2D are similar with respect to each other, as well as with respect to some features in FIGS. 1A-1D, the similar features are described briefly together. Features in individual FIGS. 2A-2D that are unique to the respective embodiment or distinct from other depicted embodiments, however, may be described explicitly and separately below for clarity.

Generally, each apparatus (200A-200D) may include:
a first tubular member (202A-202D),
a joint member (204A-204D),
a cap (206A-206D),
a manipulable member (208A-208D),
a second tubular member (210A-210D),
a connector (212A-212D),
a sampling return line (214A-214D),
length measurement indicator marks (shown on FIGS. 2D, 3A, and 3B-4E).

First Tubular Member

Inasmuch as the first tubular members 202A-202D shown in FIGS. 2A-2D may be similar to the tubular members 102A, 102C in FIGS. 1A, 1C, the details of the first tubular members 202A-202D are not reiterated again here. It is noted, however, that in order to accommodate different sizes of patients, the first tubular members 202A-202D may be detachable from the respective joint members 204A-204D to be able to adjust the length thereof. The adjustability of the tubular members is discussed in greater detail herein below.

Joint Member

In embodiments, a sampling apparatus may include a joint member 204A, as shown in FIG. 2A, which has a T-shape. Specifically, the first tubular member 202A extends from one side arm of the T-shape joint member 204A, and the second tubular member 210A extends from the other opposing side arm of the T-shape joint member 204A so as to extend collinearly with the first tubular member 202A. The sampling return line 214A, therefore, extends from the stem portion of the T-shaped joint member 204A, which is transverse to the arms of the T-shape.

In embodiments, a sampling apparatus may include a joint member 204B, as shown in FIG. 2B, where the joint member 204B may have a tubular shape so as to connect the first tubular member 202B collinearly with the sampling return line 214B. The joint member 204B may further include a hole in which the second tubular member 210B is adjoined, whereby the suction on the sampling return line 214B draws exhaled breath from both the first and second tubular members 202B and 210B.

In other embodiments, a sampling apparatus may include a joint member 204C, as shown in FIG. 2C, where the joint member 204C may be a joint that is formed at the time of manufacture, as an integral, Y-shaped union of the first and second tubular members 202C and 210C and the sampling return line 214C. In other words, the joint member 204C may not be a separate component, to which ends of the first and second tubular members 202C and 210C and the sampling return line 214C are secured, as is depicted in FIGS. 2A and 2B. Rather, instead, the merging of the first and second tubular members 202C and 210C and the sampling return line 214C may be a single component formed either entirely together or as a composite united at the time of manufacture.

Further still, in other embodiments, such as the embodiment shown in FIG. 2D, the joint member 204D is a Y-shaped component into which the ends of the first and second tubular members 202D and 210D and the sampling return line 214D are secured to one of the three branches of the Y-shaped joint member 204D.

Cap

Inasmuch as the features of the cap 206A-206D shown in FIGS. 2A-2D may be similar to the cap 106A, 106C in FIGS. 1A, 1C as depicted, the details of the cap 206A-206D are not reiterated again here. It is noted, however, that when a cap is implemented, the risk of harm to a patient may be reduced when the cap is completely affixed to the tubular member so that there is little or no chance of the cap coming off into the patient during use. For example, the cap could be glued on or otherwise formed to be permanently attached to the tubular member. Alternatively, as previously indicated, a cap may not always be implemented in every embodiment.

Manipulable Member

Manipulable members 208A-208D may be disposed, respectively, within the first tubular members 202A-202D, in a manner similar to that shown in FIG. 1C, and as described above. Thus, the details of the manipulable members 208A-208D are not reiterated again here. Note, while the manipulable members 208A-208D are depicted as not extending throughout the entire length of the respective tubular members 202A-202D and therefore differ from the manipulable member 108 shown in FIG. 1C, it is contemplated that within the depicted embodiments, the manipulable members 208A-208D may, alternatively, extend throughout an entirety of the respective tubular members 202A-202D.

Furthermore, although explicitly depicted as a distinct element for the sake of clarity, the manipulable members 208A-208D may be integral elements of the first tubular members, for example, as the actual material of the tubular members.

Additionally, in FIG. 2D, the apparatus 200D may also include a second manipulable member 218D, having characteristics like those of the first manipulable member 208D. As such, the details of the second manipulable member 218D are not reiterated here again. It is noted, however, that the ability to adjust the manipulable member 218D facilitates positioning the second tubular member 210D in a particular location, for example in a nasal mask as described with respect to FIG. 7, as may be necessary during use.

Second Tubular Member

Additionally, each of the apparatuses 200A-200D, respectively, may include a second tubular member 210A-210D, which may be coupled to the respective first tubular member 202A-202D via the respective joint member 204A-204D. In practice, the first tubular members 202A-202D may be used to sample breath exhaled via the patient's mouth, and the second tubular members 210A-210D may be used to sample breath exhaled via the patient's nose. Specific examples of how the first and second tubular members sample breath from mouth and nose, respectively, is discussed herein below with respect to FIGS. 6A-7.

Connector

In the embodiments depicted in FIGS. 2A, 2B, and 2C, the respective second tubular members 210A-210C may have disposed at the distal ends thereof connectors 212A-212C, respectively, which may be similar to the connectors 104A, 104C in FIGS. 1A, 1C. Since the second tubular members 210A-210C may sample the exhaled breath from a patient's nose, the connectors 212A-212C may be configured to connect to a corresponding connection piece on a nasal mask or hood (see FIGS. 6A and 6B discussed herein below). Further, inasmuch as the connectors 212A-212C are illustrated simply a generic box, it is contemplated that the connectors 212A-212C may be of any suitable type to form a secure connection to the nasal mask or hood, including the manners of connection described herein below with respect to the joint members/caps in FIGS. 3A-4E. For example, the connectors 212A-212C may be threaded, possibly like a Luer-Lok® connection, or may be structured to form a compression fit, an interference fit, a friction fit, or any other connection that permits a gas flow.

Figure 7:
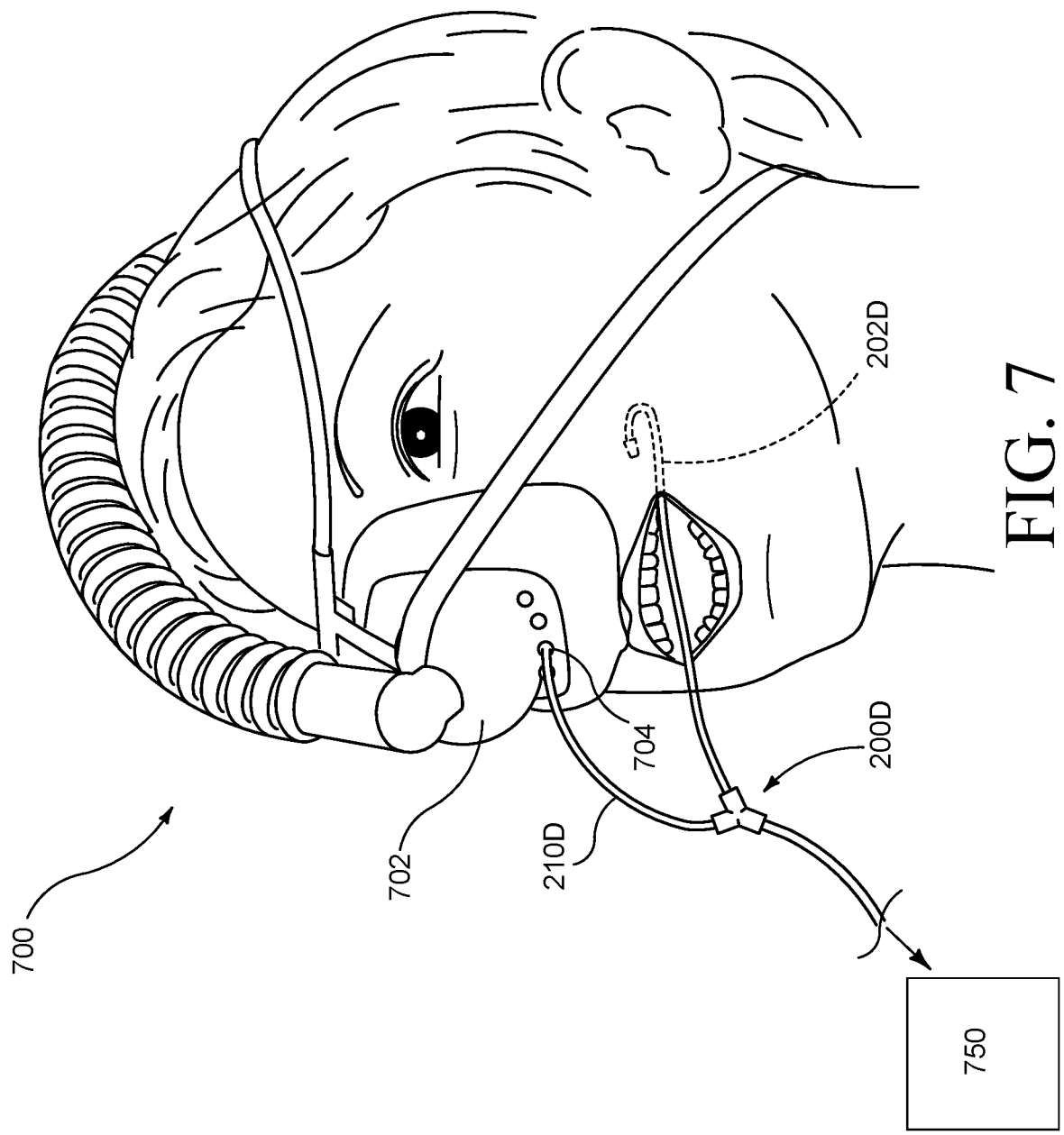
FIG. 7 illustrates an alternative example of an exhaled breath sampling apparatus connected to an existing nasal mask.

In the embodiment depicted in FIG. 2D, the connector 212D may appear similar to caps 206A-206D, however, connector 212D may function as the connection point between the apparatus 200D and a nasal mask like the one shown in FIG. 7, and therefore, is considered a connector.

Sampling Return Line

FIGS. 2A-2D also depict a sampling return line 214A-214D. The sampling return line 214A-214D may extend from the respective joint member 204A-204D to a systemic biomarker monitor device (not shown). Moreover, the suction that draws exhaled breath from the first tubular member 202A-202D to the monitor device may also draw exhaled breath from the second tubular member 210A-210D by way of the joint member 204A-204D, which joins the first and second tubular members to the respective sampling return line 214A-214D. Thusly, exhaled breath may be sampled directly from a patient's mouth and nose in order to provide a more accurate assessment of the vital statistics of a patient under anesthesia.

Length Measurement Indicator Marks

Although not illustrated on the embodiments of FIGS. 2A-2C, the length measurement indicator marks 220D shown on each of the first and second tubular members 202D and 210D may be incorporated on any of the embodiments of FIGS. 2A-2C, as well. Length measurement indicator marks 220D are shown as disposed along a portion of the length of the first and second tubular members 202D and 210D. In view of the different sizes and shapes of people who may need to undergo a procedure in which the apparatus of the instant application may be used, length measurement indicator marks 220D provide a guideline for an operator to be able adjust the length of either one or both of the first and second tubular members 202D and 210D, depending on the measured or estimated size of the mouth and distance to nasal mask of the specific patient. For example, it is possible that the original manufactured size of the apparatus may be too long for the size of the patient's mouth. In this situation, if longer first and second tubular members 202D and 210D are used, the extended length may cause the tubular members to get in the way of the operator during the procedure. Accordingly, the operator may desire to shorten the length of the first tubular member (if using an apparatus like the embodiments of FIGS. 2A-2C, for example), or one or both of the first tubular member 202D and the second tubular member 210D (if using the embodiment of apparatus 200D), to minimize any amount of excess tubing around the patient's face.

The length measurement indicator marks 220D may be marked in increments of millimeters, centimeters, decimeters, inches, or any other unit of length measurement. Further, the length measurement indicator marks 220D may be marked only on portion of the tubular members 202D, 210D, as shown in FIG. 2D, or along an entire length thereof. Alternatively, the length measurement indicator marks 220D may be disposed, for example, along either the proximal end the tubular members 202D, 210D (as shown) or the distal end the tubular members 202D, 210D, or both. Thus, an operator may measure the interior length of the distance from the back of a patient's mouth on the cheek side to the front of the patient's mouth, for example, and may shorten the total length of the apparatus 200D accordingly. Depending on the embodiment used for the apparatus, shortening the length of the tubular member(s) may be accomplished by many ways, including cutting, bending, breaking, snapping, sliding, etc.

In order to minimize the excess tubing, the following steps may be followed. A side of the patient's cheek or the length along the patient's teeth in the mouth may be measured. The first tubular member 202D from the connector 204D. Then, using the length measurement indicator marks 220D, the operator may shorten the first tubular member 202D to adjust the length thereof for the smaller size patient. By shortening the first tubular member 202D, the operator may be able to avoid having excess tubing potentially getting in the way of the work being done on the patient. With regard to the second tubular member 210D, since the second tubular member 210D may be inserted into a hole in a nasal mask, for example, like the one shown in FIG. 7, the operator may measure the distance between the joint member 204D and the hole in the nasal mask on the patient's face. Then, the operator may similarly shorten the second tubular member 210D, if necessary to accommodate a smaller distance as well.

Illustrative Embodiments of Connections at Joint Members and Caps

Due to the potential need to shorten the tubular members of the apparatus depending on the size of the patient, a manner of easily, effectively, and safely disconnecting and reconnecting the tubular members to either or both of the connectors and caps may be desirable. Inasmuch as a removable cap may pose a health risk to the patient, it may be preferable to not have the cap be removable. However, it is contemplated that the cap may be fixable such that, after adjusting a length of the tubular members, the cap may be replaced and fixed to the tubular member via a fastening means such as adhesive, means shown in the figures, or other means so as to ensure that the cap does not inadvertently get inside the patient.

FIGS. 3A-3E depict different embodiments of potential connection types that may be used to connect proximal ends of a tubular member (302A-302E) to a connector (304A-304E) of an apparatus (300A-300E) of the instant application. Notably, FIGS. 4A-4E are placed adjacent to the respective FIGS. 3A-3E to depict corresponding connection types between the distal ends of a tubular member (402A-402E) and a cap (404A-404E). Therefore, the descriptions of the connections between the joint members 304A-304E and the tubular members 302A-302E, and the connections between the tubular member 402A-402E and the cap 404A-404E may be substantially similar and are therefore discussed together.

Figure 4A:
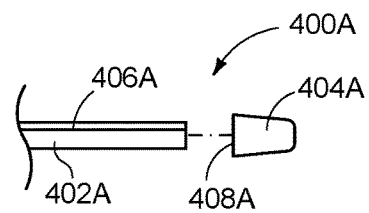
FIG. 4A illustrates an exploded, side view of an example of a distal end of a tubular member of an exhaled breath sampling apparatus.

For the sake of simplicity and clarity in the drawings, of the embodiments in FIGS. 3A-4E, only the embodiment in FIG. 4A is actually depicted with the tubular member 402A having a manipulable member 406A. Regardless, it is understood that one or both ends of the tubular members illustrated in FIGS. 3A-3E and 4B-4E may incorporate a manipulable member. Additionally, it is noted that in an embodiment where a tubular member of an apparatus may be removable from both the joint member on the proximal end and the cap on the distal end, the type of connections used to join the adjacent parts may be different from each other and need not be the same type.

Specifically, FIGS. 3A and 4A depict an exploded view of a generic tubular member 302A, 402A aligned with a generic joint member 304A and cap 404A, respectively. In FIG. 3A, the tubular member 302A has thereon length measurement indicator marks 306A, while (as mentioned above), FIG. 4A depicts a manipulable member 406A. Additionally, the joint member 304A and cap 404A each are labeled with a reference to an opening 308A and 408A, respectively.

For convenience, a list of corresponding reference numbers with respect to the common components is provided here. Namely, FIGS. 3B-3E and 4B-4E include a tubular member 302B-302E, 402B-402E, which have thereon length measurement indicator marks 306B-306E, 406B-406E. FIGS. 3B-3E further include a joint member 304B-304E on the proximal end of the tubular member 302B-302E, respectively, and the joint member 304B-304E is depicted as having attached thereto a secondary tubular member 312B-312E, which may serve as a nasal sampling tubular member. Also depicted in FIGS. 3B-3E and 4B-4E is a connection component 310B-310E and 410B-410E, respectively. The connection components 310B-310E, 410B-410E are discussed in more detail below, however, inasmuch as the manner of connection depicted between the joint members 304B-304E and the respective tubular members 302B-302E is substantially the same as that between the tubular members 402B-402E and respective caps 404B-404E, the connection components 310B-310E, 410B-410E are explained once for simplicity with respect to the components as they are referenced in FIGS. 3B-3E. Any significant differences between the connections formed by the connection components 310B-310E and the connection components 410B-410E are explained accordingly.

Figure 3B:
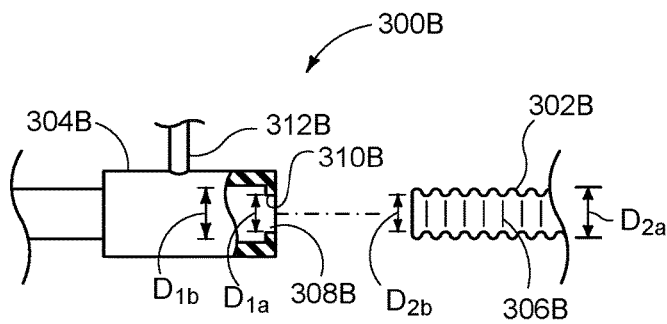
FIG. 3B illustrates an exploded, partial-cross-sectional side view of another example of a proximal end of a tubular member of an exhaled breath sampling apparatus.
Figure 4B:
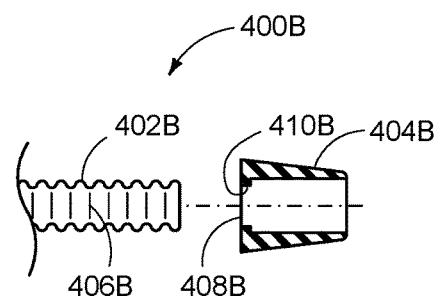
FIG. 4B illustrates an exploded, partial-cross-sectional side view of another example of a distal end of a tubular member of an exhaled breath sampling apparatus.

In an embodiment according to FIG. 3B, the connection component 310B may include a flange extending radially, inwardly from an inside wall edge of the distal end of the joint member 304B. Likewise, in FIG. 4B the connection component 410B may include a flange extending radially, inwardly from an inside wall edge of the proximal end of the cap 404B. At least a portion of the length of the outer surface of the tubular member 302B may be shaped to have a side profile that appears like a series of alternating annular ridges and valleys (or a wave-shaped formation, ribs, etc.). In order to maintain the tubular member 302B securely within the respective joint member 304B, the diameter $D_{1a}$ of the opening 308B is less than a diameter $D_{2a}$ of the "ridges," and greater than, or approximately equal to, the diameter $D_{2b}$ of the "valleys." Moreover, the diameter $D_{2b}$ of the interior of the joint member 304B behind the flange (connection component 310B) is greater than the diameter $D_{1a}$ of the opening 308B, so as to accommodate the ridges of the tubular member 302B. Furthermore, a thickness (or width) of the flange 310B approximates the length of the valleys, which is the distance between ridges, so that the flange securely holds the tubular member 302B. The connection formed by connection component 410B As such, when an end of the tubular member 302B, 402B is inserted into the joint member 304B or cap 404B, the tubular member 302B, 402B flexes slightly so that the ridges push past the flange of the connection component 310B, 410B, and the flange surrounds a valley held in between two ridges, thereby securing the tubular member 302B, 402B. Additionally, the operator may use the length measurement indicator marks 306B to determine how much of the tubular member 302B, 402B may be shortened, if needed.

Figure 3C:
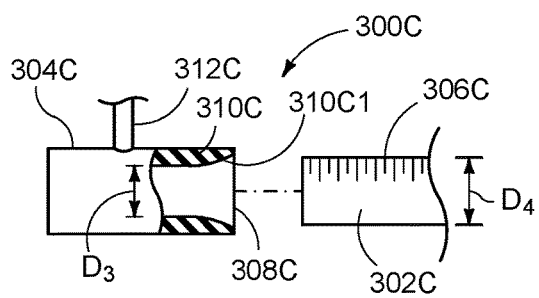
FIG. 3C illustrates an exploded, partial-cross-sectional side view of another example of a proximal end of a tubular member of an exhaled breath sampling apparatus.
Figure 4C:
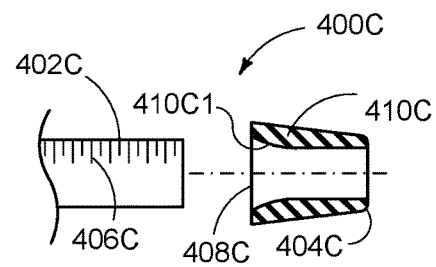
FIG. 4C illustrates an exploded, partial-cross-sectional side view of another example of a distal end of a tubular member of an exhaled breath sampling apparatus.

In FIGS. 3C and 4C, a compression fit is illustrated as the connection component 310C, 410C. In particular, the diameter $D_3$ of the interior of the joint member 304C may be less than the outer diameter $D_4$ of the tubular member 302C. As such, when an end of the tubular member 302C is pressed into the joint member 304C, the tubular member 302C may be secured by compression in the joint member 304C. Further, connection component 310C may also include a tapered edge 310C1 at the entry to the joint member 304C, so as to ease the insertion process between the tubular member 302C and the joint member 304C. The embodiment of the connection component 410C with tapered edge 410C1 between tubular member 402C and cap 404C of FIG. 4C may connect similarly as is depicted and described above with respect to FIG. 3C.

Figure 3D:
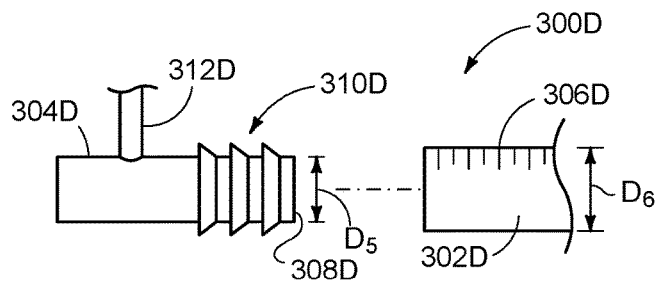
FIG. 3D illustrates an exploded, side view of another example of a proximal end of a tubular member of an exhaled breath sampling apparatus.
Figure 4D:
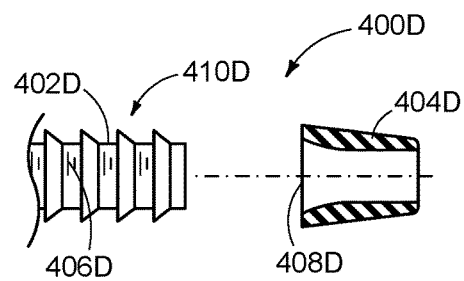
FIG. 4D illustrates an exploded, partial-cross-sectional side view of another example of a distal end of a tubular member of an exhaled breath sampling apparatus.

In FIGS. 3D and 4D, an interference fit is implemented as the manner of connection between the tubular members 302D, 402D and the respective joint member 304D and cap 404D. Interference may be created between at least one or more (as a series) of the connection components 310D, 410D and the interior wall of the tubular member 302D and the cap 304D, respectively. Note, that while the connection components 310D are depicted in FIG. 3D as disposed on an exterior side of the joint member 304D, the connection components 410D are depicted in FIG. 4D as disposed on an exterior side of the tubular member 402D, having measurement indicator marks disposed therebetween. Regardless, the connection components 310D, 410D function similarly. In particular, connection component 310D may include one or more annular, frustoconical-shaped flanges on an exterior surface of the distal end of the joint member 304D. An outer diameter of the frustoconical-shaped flange(s) (connection component 310D) may be larger than the outer diameter $D_5$ of the joint member 304D and smaller than the diameter $D_6$ of outer surface of the tubular member 302D, such that, when the tubular member 302D is pressed against the joint member 304D, the frustoconical-shaped flanges 310D interfere with the inner wall of the tubular member 302D, flexing against the wall so as to secure the tubular member 302D to the joint member 304D. The embodiment of the connection component 410D between tubular member 402D and cap 404D of FIG. 4D may connect similarly as is depicted and described above with respect to FIG. 3D. Moreover, the cap 404D may include a tapered edge at the opening 408D to ease insertion of the frustoconical flange(s) 410D.

Figure 3E:
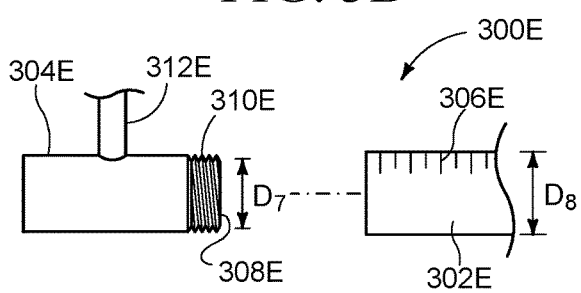
FIG. 3E illustrates an exploded, side view of yet another example of a proximal end of a tubular member of an exhaled breath sampling apparatus.
Figure 4E:
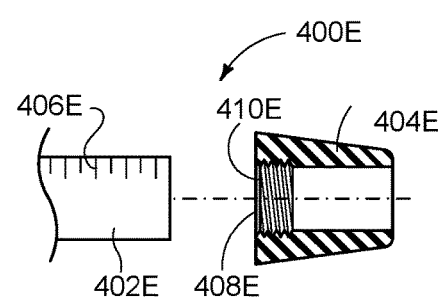
FIG. 4E illustrates an exploded, partial-cross-sectional side view of another example of a distal end of a tubular member of an exhaled breath sampling apparatus.

In example embodiments, as pictured in FIGS. 3E and 4E, the connection components 310E, 410E may include a threaded surface to make a connection between the tubular member 302E, 402E and the respective joint member 304E and cap 404E. For example, in the embodiment of FIG. 3E, the distal end of the joint member 304E may have a threaded surface, with the diameter $D_7$ of the threads on the joint member 304E being larger than the inner diameter of the tubular member 302E and smaller than the diameter $D_8$ of the outer surface of the tubular member 302E. While the interior surface of the tubular member 302E may be threaded to assist in securing the joint member 304E, it need not be threaded, as the threads 310E may be sufficiently sharp and rigid to bite into the material of the tubular member 302E when the tubular member 302E is rotated over the joint member 304E. Alternatively, as shown in FIG. 4E, instead of having threads on the outer surface of the connecting element, the inner surface of the cap 404E is threaded. The smallest diameter of the threaded surface may be smaller than the outer diameter of the distal end of the tubular member 402E, so that the threads inside the cap 404E bite into the outer surface of the tubular member 402E when the cap 404E is rotated about the tubular member 402E, thereby securing the cap 404E to the tubular member 402E.

Accordingly, as depicted in FIGS. 3E and 4E, a joint member and/or a cap may have internal or external threads, whereby the tubular member may be secured after sizing.

Illustrative Alternative Embodiment of an Adjustable Sampling Apparatus

Figure 5:
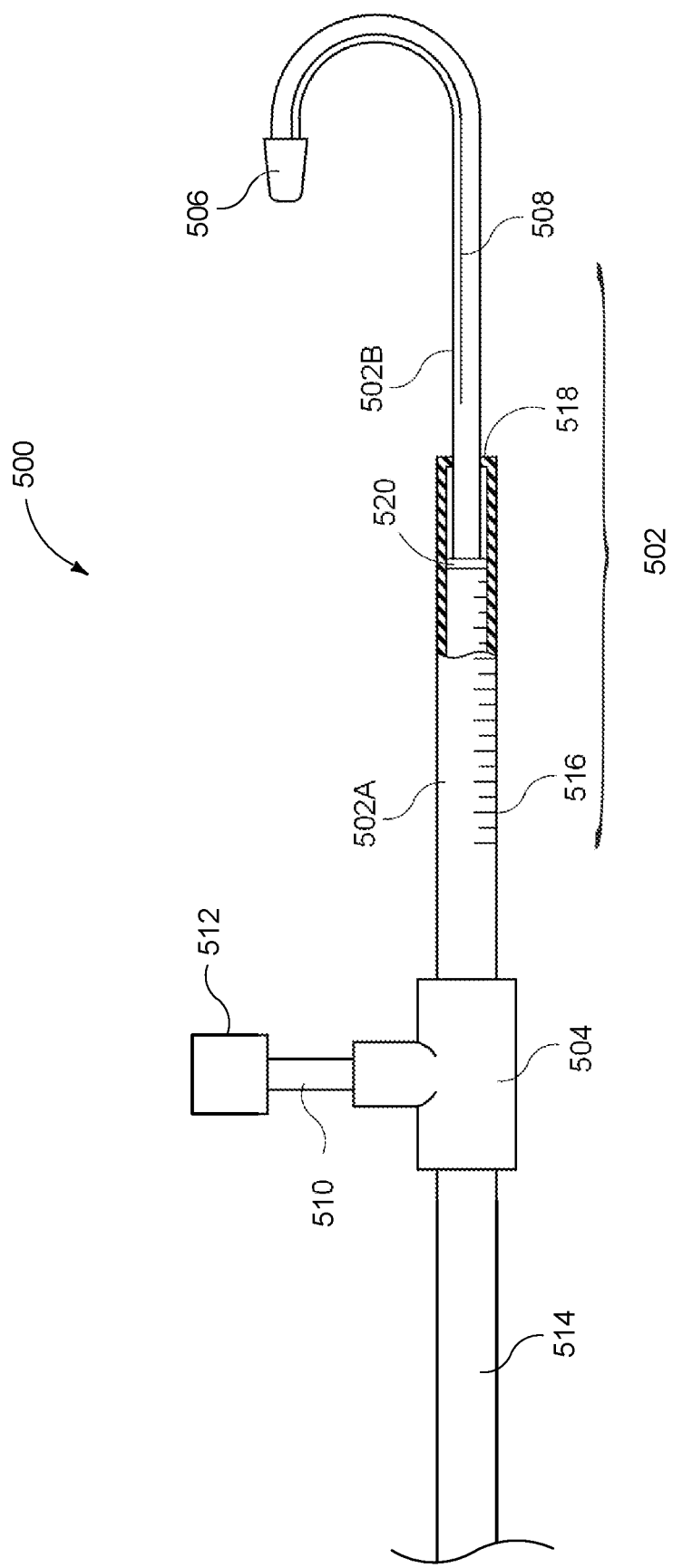
FIG. 5 illustrates a partial-cross-sectional side view of another example of an exhaled breath sampling apparatus.

FIG. 5 depicts a partial cross-sectional view of an alternative embodiment of an adjustable sampling apparatus 500 that may include a first tubular member 502 having a distinct proximal portion 502A and a distinct distal portion 502B. The partial cross-section is of the end of the proximal portion 502A so as to clearly depict the slidable aspect of this embodiment.

The proximal portion 502A may extend from the joint member 504. The distal portion 502B may be slidably insertable within the proximal portion 502A. A cap 506 may be attached to the distal portion 502B, and a manipulable element 508 may be an integral part of, disposed on, or disposed within the distal portion 502B. (The manipulable element 508 is only depicted as a visible "component" within the distal portion 502B as a representation of the ability to manipulate the distal portion 502B, and is not intended to exclude an embodiment of the material of the tubular member itself being the manipulable element 508.) As in other embodiments, a second tubular member 510 may be attached to the joint member 504, and the second tubular member 510 may have attached thereto a connector 512. The connector 512 may connect to a nasal hood or mask (not shown). Further, the sampling return line 514 may connect to the joint member 504, as well. The first tubular member 502 may also have thereon length measurement indicator marks 516, which are used to visualize the amount of adjustment of the length of the apparatus 500.

With regard to the manner of adjusting the length of the embodiment of FIG. 5, FIG. 5 depicts a first sliding component 518 and a second sliding component 520. The first sliding component 518 may include a flange extending radially, inwardly from an inside wall edge of the proximal portion 502A of the first tubular member 502. The second sliding component 520 may include a flange extending radially, outwardly from an outside wall edge of the distal portion 502B of the first tubular member 502. A desired length position between the proximal portion 502A and the distal portion 502B may be maintained by a frictional interference force between the inner wall surface of the proximal portion 502A and the outer peripheral surface of the flange of the second sliding component 520 on the distal portion 502B.

Inasmuch as the distal portion 502B may be slidable within the proximal portion 502A, a distal surface of the flange of the second sliding component 520 opposes the proximal surface of the first sliding component 518, such that the first and second sliding components 518, 520, respectively are in abutment with each other in a fully extended position so as to prevent removal of the distal portion 502B entirely from the proximal portion 502A. Further, the second sliding component 520 is free to slide from the position of abutment in a direction toward the proximal side of the apparatus 500 so as to shorten a length of the apparatus 500. Sliding may be achieved by pressing or pulling the proximal portion 502A and distal portion 502B with respect to each other, where the pressing or pulling force is a level of force greater than the level of frictional force between the inner wall surface of the proximal portion 502A and the outer peripheral surface of the flange of the second sliding component 520. Additionally, in view of the ability to slide the distal portion 502B within the proximal portion 502A, a material of at least the proximal portion 502A may be transparent or translucent so as to permit an operator to view the interior of the proximal portion 502A and see the end of the distal portion 502B within the proximal portion 502A against the length measurement indicator marks 516, thereby facilitating a length adjustment.

Figure 6A:
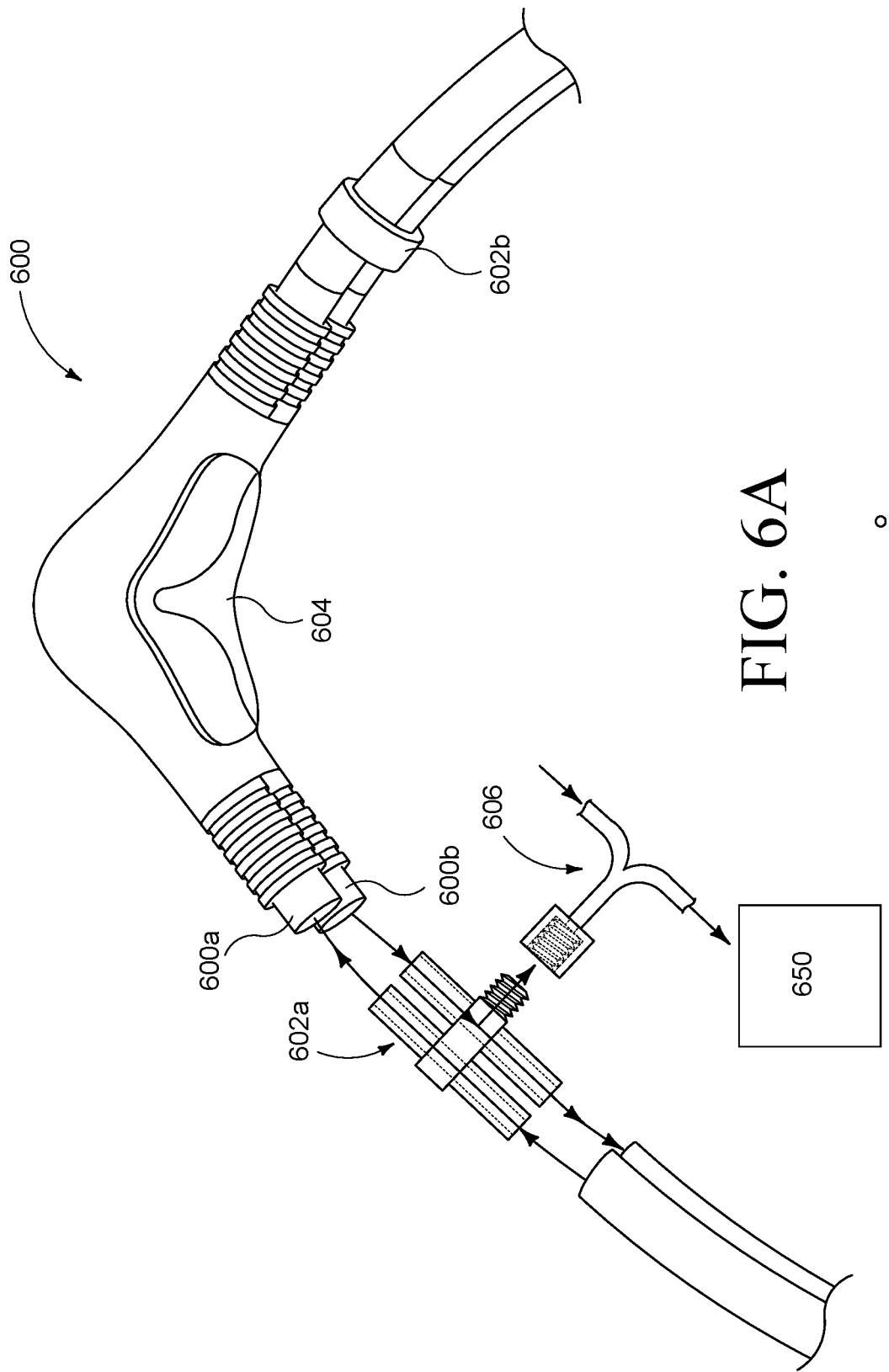
FIG. 6A illustrates an example of a modified connector used in an existing nasal hood so as to permit connection of an exhaled breath sampling apparatus.

Illustrative Example of an Embodiment of a Sampling Apparatus in Connection with a Nasal Hood An example of a nasal hood to which the sampling apparatus of the instant application may be coupled is the Porter Double Mask Scavenger Breathing Circuit ("nasal hood") marketed by Porter Instrument Division of Parker Hannifin. FIG. 6A depicts the nasal hood 600 that may include a modified connector 602a, a standard connector 602b, and a nose port 604. As depicted, the nasal hood 600 may further include a line-in 600a via which gas may be administered to a patient through the nose port 604 when in position over a patient's nose, and a line-out 600b via which exhaled breath from a patient's nose may be suctioned out. (See the arrows indicating flow in and out of the nasal hood 600 on the modified connector 602a.)

Also depicted in FIG. 6A is a portion of an example sampling apparatus 606, which may connect to the modified connector 602a to sample the exhaled breath from the patient's nose as the breath passes from the line-out 600b through the modified connector 602a (explained in more detail with respect to FIG. 6B). The exhaled breath may be sampled via the sampling return line that leads to a systemic biomarker sampling device 650. Note that the depicted embodiment of the example sampling apparatus 606 may resemble the embodiment illustrated in FIG. 2C, (i.e., the integral Y-shaped joint member 204C with connector 212C resemble the portion of the example sampling apparatus 606). Any such resemblance is coincidental and it is contemplated that any of the aforementioned embodiments of sampling apparatuses may couple with the modified connector 602a, including, for example, the embodiments of FIGS. 1A, 1C, and 2A-2D. If the embodiment of FIG. 1A or 1C is coupled to the modified connector 602a, it is contemplated that the line out 600b may be connected also to a systemic biomarker sampling device (such as device 650) in order to sample exhaled breath from the mouth and nose. Furthermore, while the modified connector 602a is illustrated with a threaded port (discussed further with respect to FIG. 6B) that corresponds to the threaded connector (for example, a Luer-Lok® connector) on the example sampling apparatus 606, it is contemplated that the port may be modified to securely engage a cap such as the connector 212D in the embodiment of FIG. 2D.

The modified connector 602a is illustrated in more detail in FIG. 6B. In particular, the modified connector 602a may include a line-in tube (or line-in tube segment) 608 and a line-out tube (or line-out tube segment) 610, which adjoin the line-in 600a and the line-out 600b on nasal hood 600, respectively. A coupler (or line coupler) 612 holds the line-in tube 608 and the line-out tube 610 together in a fixed position. At a base (or base area) of the coupler 612, a sample joint tube (or sample tube segment) 614 extends through (or intersects) the coupler 612 to the line-out tube 610. The end of the sample joint tube 614 includes a threaded exterior surface 616 in order to connect the example sampling apparatus 606. As noted above, however, the sample joint tube 614 may be configured with a secure connection means other than a threaded surface. That is, the coupler 612 and the line-out tube 610 each have a co-aligned hole 618 in which the sample joint tube 614 is disposed so as to form an additional passageway out of the line-out tube 610 for sampling the breath (note the dashed-arrow line passing from the line-out 610 to the sample joint tube 614.

Thus, with the Porter Double Mask Scavenger Breathing Circuit, an operator may replace the standard connector 602b with a modified connector 602a according to this application, and thereby connect a sampling apparatus. The modified connector 602a provides an operator with the ability to sample the systemic biomarkers in the exhaled breath from both the nose and the mouth simultaneously.

Illustrative Example of an Embodiment of a Sampling Apparatus in Connection with a Nasal Mask Another example of a nasal mask to which the sampling apparatus of the instant application may be coupled is the Safe Sedate® 700 ("nasal mask") depicted in FIG. 7. In embodiments, the nasal mask 700 may include a nose port 702, which has one or more exhaust holes 704. As illustrated, the nasal mask 700 may be strapped to a patient's face so that the mouth is clearly accessible. FIG. 7 further depicts an example of a sampling apparatus 200D (FIG. 2D) being connected to the nasal mask 700. In particular, the sampling apparatus 200D may include a first tubular member 202D and a second tubular member 210D, and the sampling apparatus 200D may draw exhaled breath to a systemic biomarker sampling device (such as device 750). The first tubular member 202D may be manipulated to have a shape and size so that the first tubular member 202D is inserted out of the way in the patient's mouth. Specifically, the first tubular member 202D may form a hook shape such that the distal end thereof may be placed around the back of the teeth in the patient's mouth, and the proximal end may extend along a side of the teeth next to the cheek. Further, the second tubular member 210D may be sized and positioned so as to be able to insert the connector ("cap") on the distal end of the second tubular member 210D into an exhaust hole 704 of the nasal mask 700. As stated above with respect to the cap in FIGS. 1A and 1C, the cross-sectional area of the proximal end of the cap may be larger than the cross-sectional area of the distal end of the cap. Further, the cross-sectional area (i.e., diameter) of the exhaust hole 704 may be smaller than the cross-sectional area of the distal end of the cap. Inasmuch as the material of the nasal mask and/or the material of the cap has elastic properties, an operator may force the cap on the distal end of the second tubular member 210D through the exhaust hole 704. Due to the flexing of the material under force, once the proximal side of the cap has squeezed through the narrow area of the hole 704, the material is released from force and resumes its original shape. Thus, after inserting the cap through the exhaust hole, the wider surface area of the cap surrounding the tubular member may act as a backstopping surface against an inside surface of the nasal mask near the edge of the hole 704, and may prevent accidental removal of the tubular member.

Thus, the embodiment of sampling apparatus 200D in FIG. 2D is well-suited for connection to the Safe Sedate® nasal mask 700. However, it is contemplated that nasal mask 700 may be modified to include a different means of connection, such as a threaded port, to accommodate a different embodiment of the sampling apparatus.

Figure 8:
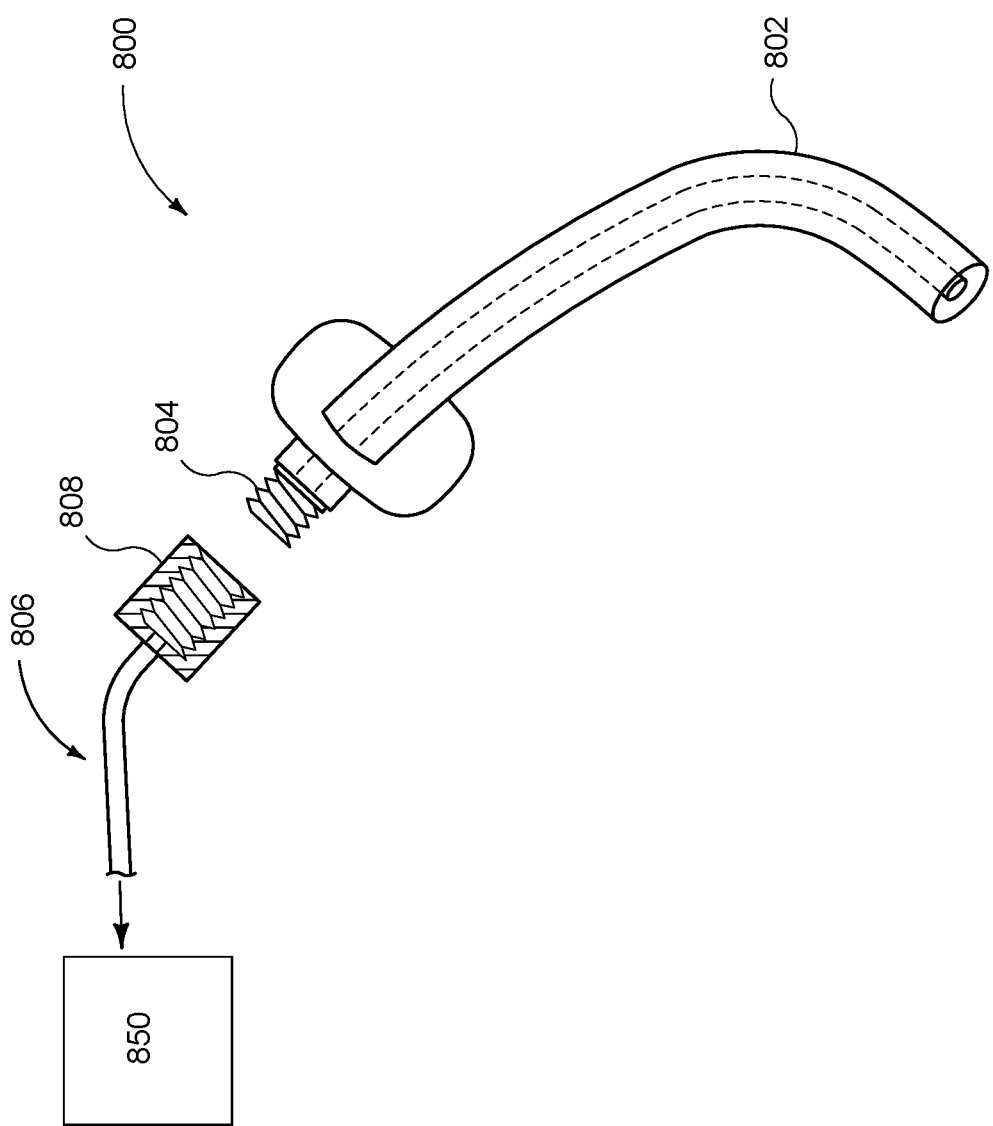
FIG. 8 illustrates a perspective view of an alternative example of an exhaled breath sampling apparatus.

Illustrative Example of an Embodiment of a Sampling Apparatus in Connection with an Oral Airway In yet another embodiment of how a sampling apparatus may be coupled with a product to sample a patient's exhaled breath, FIG. 8 shows an oral airway 800 having a tube portion 802 (that sits in the patient's mouth) modified with a threaded end 804. The threaded end 804 may be configured to connect to a sampling apparatus 806 via a connector 808, which may be similar to a Luer-Lok® connection, for example, or may be any other type of connection between the sampling apparatus and the oral airway 800. Thus, the oral airway 800 may be inserted into a patient's mouth, and the exhaled breath may be sampled in a systemic biomarker sampling device (such as device 850) via the sampling apparatus 806.

Figure 9A:
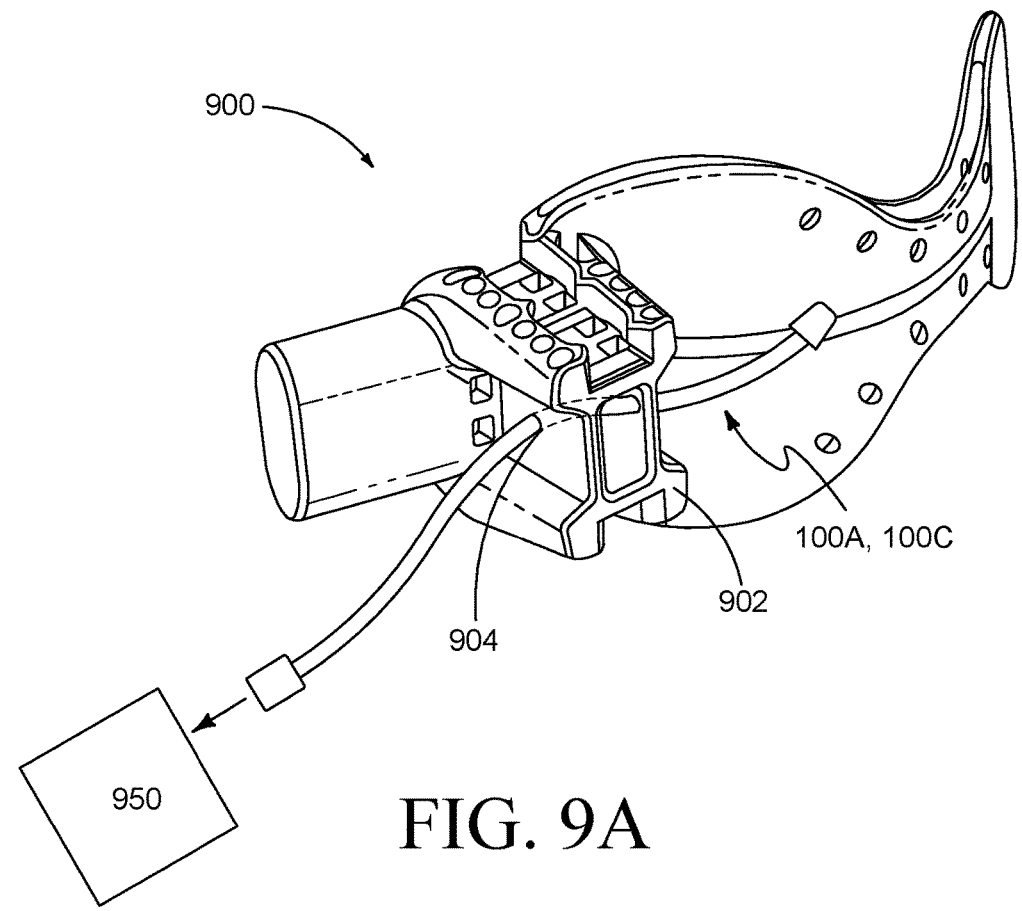
FIG. 9A illustrates a perspective view of an alternative example of an exhaled breath sampling apparatus paired with an existing dental product.
Figure 9B:
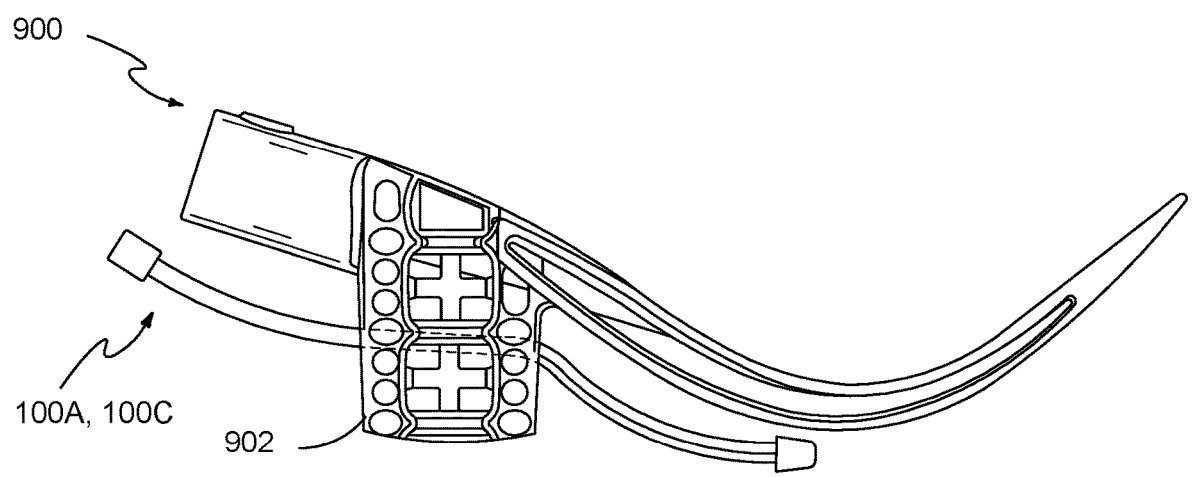
FIG. 9B illustrates a top cross-sectional view of the alternative example of the exhaled breath sampling apparatus in FIG. 9A.

Illustrative Example of an Embodiment of a Sampling Apparatus in Connection with an Isolite® System In yet another manner of how a sampling apparatus may be coupled with a product to sample a patient's exhaled breath, FIGS. 9A and 9B depict a perspective view and a top view of an Isolite® system 900 ("system") that has been modified to accommodate the addition of an example sampling apparatus 100A, 100C, as depicted in FIGS. 1A, 1C. Alternatively, FIGS. 9C and 9D illustrate integrated embodiments, as discussed in detail below.

Using an integral bite block 902 for the patient to bite down onto with one side of the patient's teeth, the system 900 is a device used in dental practice to provide light and/or suction to a patient's mouth during a procedure. In FIGS. 9A and 9B, the system 900 is depicted as modified to include a hole 904 through the bite block 902. The tubular member of the example sampling apparatus 100A, 100C is disposed through the hole 904 so that the distal end of the tubular member may be located behind the system 900 in the back of the patient's mouth when the system 900 is in place in a patient's mouth. Accordingly, the sampling apparatus 100A, 100C is out of the way of the dental work.

It is noted that the hole 904 was placed in the bite block 902 for convenience and simplicity in the drawings, as well as convenient and simple placement in manufacturing. However, it is contemplated that the hole 904 may be placed through or within any other portion of the system so as to quickly, conveniently, and safely sample systemic biometrics at sampling device 950. For example, the system 900 may include a sampling line that is embedded within a portion of the main body of the system 900, as shown in FIGS. 9C and 9D.

Figure 9C:
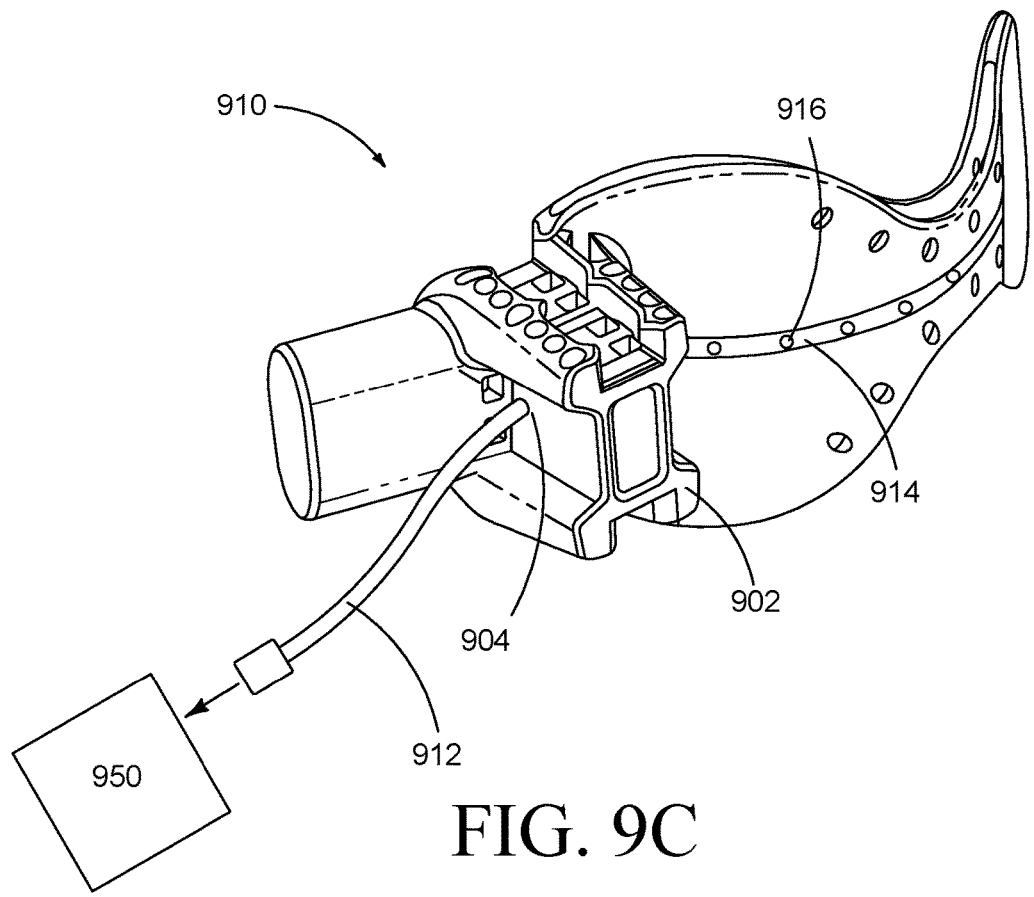
FIG. 9C illustrates a perspective view of an alternative example of an exhaled breath sampling apparatus paired with an existing dental product.
Figure 9D:
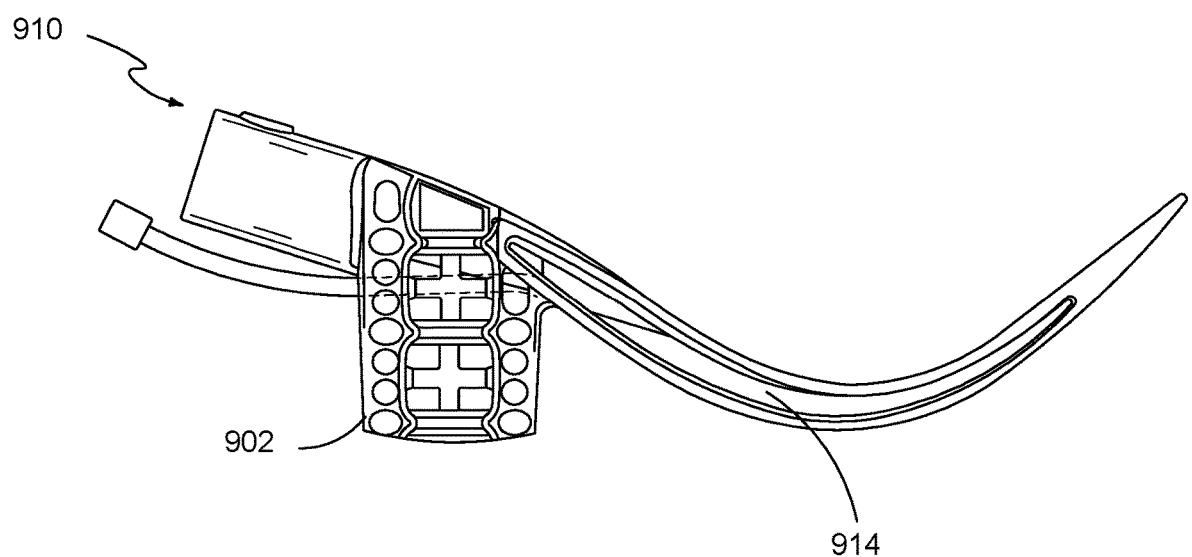
FIG. 9D illustrates a top cross-sectional view of the alternative example of the exhaled breath sampling apparatus in FIG. 9C.

In the embodiment shown in FIGS. 9C and 9D, the system 910 may have a sampling return line 912 extending from a portion of the bite block 902 in a position such that the sampling return line 912 extends through hole 904 into a rib 914 in the main body of the system 910. The rib 914 may include holes 916 (fenestrations) through the surface of the system 910, spread along the length of the rib 914 so as to be able to sample breath from the patient.

Figure 10:
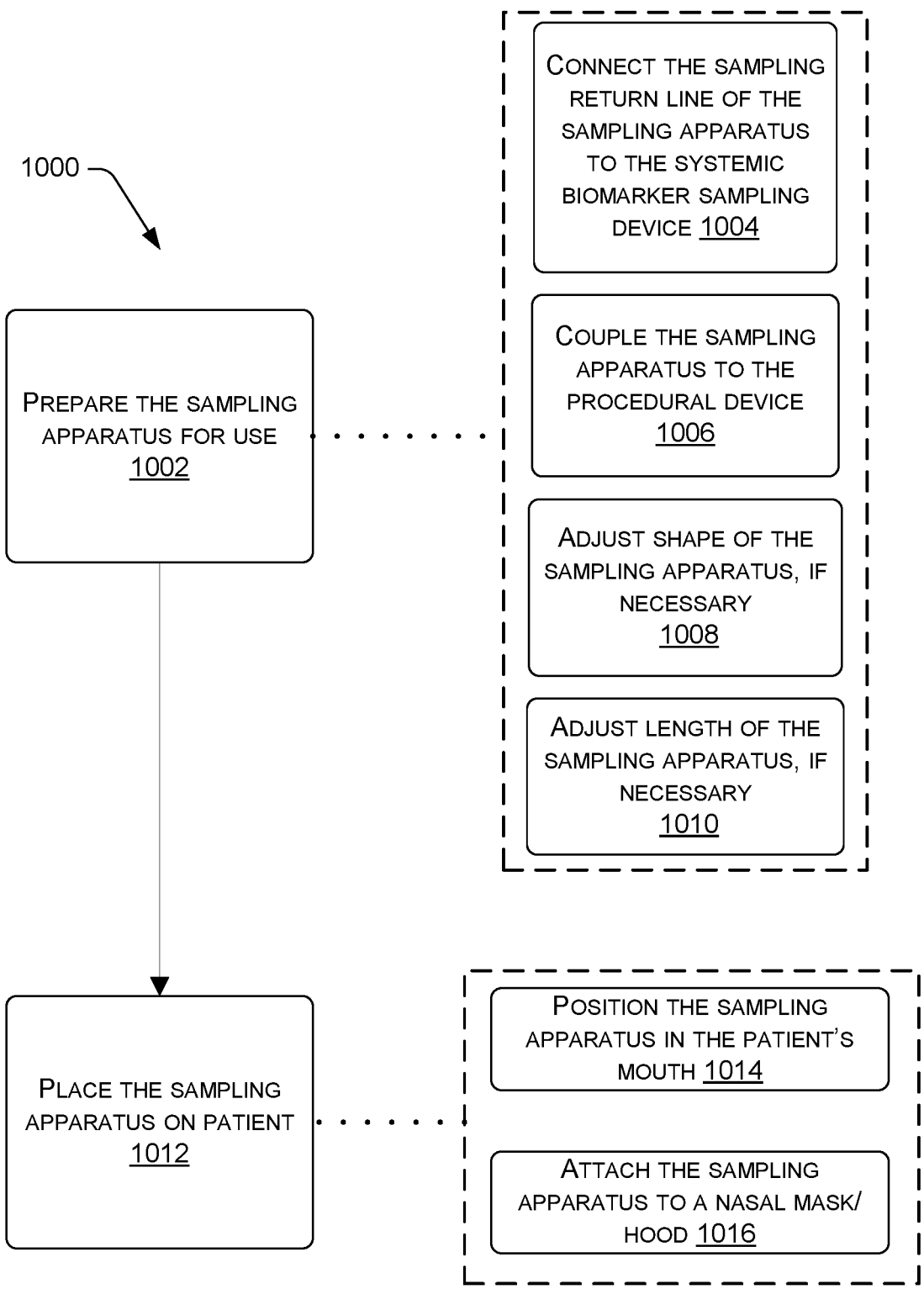
FIG. 10 illustrates an example of a method of monitoring systemic biomarkers according to the instant application.

Illustrative Method of Preparing to Sample a Patient's Exhaled Breath During a Procedure In embodiments of the instant application, the steps as shown in FIG. 10 may be performed as a method 1000 to prepare to sample a patient's exhaled breath during a procedure. Step 1002 indicates that the operator may prepare the sampling apparatus for use. Specifically, and in no particular order, the preparation in step 1002 may further include a step 1004 of connecting the sampling return line of the sampling apparatus to the systemic biomarker sampling device. In step 1006, the operator may couple the sampling apparatus to a procedural device. In step 1008, the shape of the sampling apparatus may be adjusted to accommodate the size of the patient, and likewise, in step 1010, the length of the sampling apparatus may also be adjusted. Steps 1008 and 1010 may further include measuring the patient and accordingly adjusting the sampling apparatus, which may include one or more of bending, cutting, breaking, snapping, sliding, or otherwise adjusting the length or shape of the tubular member(s). When the sampling apparatus is ready, the operator may perform step 1012 of placing the sampling apparatus on the patient. Step 1012 may further include a step 1014 of positioning the sampling apparatus in the patient's mouth. Further, if applicable, the operator may also perform step 1016 which is to attach the sampling apparatus to a nasal mask or hood.

CONCLUSION

Although several embodiments have been described in language specific to structural features and/or methodological acts, it is to be understood that the claims are not necessarily limited to the specific features or acts described. Rather, the specific features and acts are disclosed as illustrative forms of implementing the claimed subject matter.

What is claimed is:

1. A connector device, comprising:
   a line coupler including a first coupling portion and a second coupling portion;
   a line-in tube segment extending through the first coupling portion of the line coupler so as to extend from both sides thereof;
   a line-out tube segment extending through the second coupling portion of the line coupler so as to extend from both sides thereof, an axis of the line-in tube segment being distinct and non-coaxial from an axis of the line-out tube segment; and
   a sample tube segment disposed in a base area of the line coupler, the sample tube segment intersecting only the line-out tube segment to create a flow path from the line-out tube segment into the sample tube segment,
   wherein the line coupler holds the line-in tube segment and the line-out tube segment together in parallel, and
   wherein the line-in tube segment and the line-out tube segment are fixed in place within the first coupling portion and the second coupling portion, respectively.

2. The connector device according to claim 1, wherein the sample tube segment has a threaded portion on an end thereof, the end extending in a direction away from the line coupler.

3. The connector device according to claim 2, wherein the threaded portion of the sample tube segment is threaded to accommodate a luer taper thread configuration.

4. The connector device according to claim 1, wherein the first coupling portion is disposed parallel with the second coupling portion.

5. The connector device according to claim 1, wherein the sample tube segment extends in a direction transverse to a direction of extension of the line-out tube segment.

* * * * *